United States Patent
Simon et al.

(10) Patent No.: US 6,353,118 B1
(45) Date of Patent: Mar. 5, 2002

(54) DEWATERING AND PURIFICATION OF CRUDE PYRROLIDINE

(75) Inventors: Joachim Simon, Mannheim; Peter Wahl, Ladenburg; Willi Schmidt, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/716,835

(22) Filed: Nov. 20, 2000

(30) Foreign Application Priority Data

Nov. 30, 1999 (DE) .......................... 199 57 672

(51) Int. Cl.$^7$ .......................... C07O 295/023
(52) U.S. Cl. .......................... 548/579
(58) Field of Search .......................... 548/579

(56) References Cited

U.S. PATENT DOCUMENTS 4,739,051 A  4/1988  Schroeder .................. 544/100
5,502,213 A  * 3/1996  Pfab et al. .................. 548/564

FOREIGN PATENT DOCUMENTS

EP   070 397   1/1983

* cited by examiner

*Primary Examiner*—Mukund J. Shah
*Assistant Examiner*—Thomas C McKenzie
(74) *Attorney, Agent, or Firm*—Keil & Weinkauf

(57) ABSTRACT

In a process for purifying crude pyrrolidine to give a pyrrolidine composition comprising more than 99% (m/m) of pyrrolidine and less than 0.3% (m/m) of water, crude pyrrolidine comprising from 40 to 98% (m/m) of pyrrolidine and having a water content of more than 2% (m/m) is subjected to continuous distillation at a pressure at the top of less than 950 hPa in a column having a stripping section and a rectifying section.

6 Claims, No Drawings

DEWATERING AND PURIFICATION OF CRUDE PYRROLIDINE

The present invention relates to a process for dewatering and purifying crude pyrrolidine. The process product is anhydrous pyrrolidine, i.e. pyrrolidine having a water content of less than 0.3% and a pyrrolidine content of more than 99% (percentages are always by weight).

Anhydrous pyrrolidine is a valuable intermediate and is employed, for example, in the synthesis of crop protection agents and pharmaceuticals.

Pyrrolidine is nowadays prepared predominantly by reaction of butanediol with ammonia using a nickel/copper catalyst. Such a process is described in EP 0 070 397 A1 (U.S. Pat. No. 4,739,051). The crude pyrrolidine prepared by this process contains, in addition to traces of low-boiling impurities such as tetrahydrofuran (THF), high boilers such as N-butylpyrrolidine, N-(4-aminobutyl)pyrrolidine and 1,4-bis(N-pyrrolidino)butane and 40% of water which is formed in the reaction according to the equation [1]:

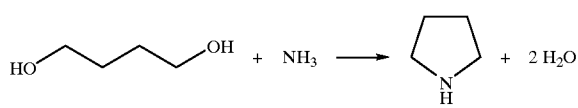

[1]

Although pyrrolidine does not form an azeotrope with water at atmospheric pressure, the removal of water has proved to be problematical.

Hitherto, 50% strength aqueous sodium hydroxide has been added to the crude pyrrolidine in such an amount that the mixture has a sodium hydroxide concentration of 25%. After intensive mixing, the upper organic phase is separated off. This phase comprises pyrrolidine plus 3–5% of water which has hitherto been removed by azeotropic distillation using hexane as entrainer. The anhydrous pyrrolidine obtained in this way was subsequently fractionally distilled, giving pure pyrrolidine having a water content of less than 0.3%. Dewatering by means of azeotropic distillation is extraordinarily time-consuming and thus costly. In addition, the known process comprises three process steps, two of them being separate distillation procedures, which leads to an increased outlay in terms of apparatus and corresponding yield losses.

It is an object of the present invention to provide a process for dewatering and purifying crude pyrrolidine which gives anhydrous and in-specification pyrrolidine (max. water content: 0.3%, min. pyrrolidine content: 99%) in one distillation step.

The achievement of this object starts out from a process for purifying crude pyrrolidine to give a pyrrolidine composition comprising more than 99% (m/m) of pyrrolidine and less than 0.3% (m/m) of water.

In the process of the present invention, crude pyrrolidine comprising from 40 to 98% (m/m) of pyrrolidine and having a water content of more than 2% (m/m) is subjected to continuous distillation at a pressure at the top of less than 950 hPa in a column having a stripping section and a rectifying section.

The process of the present invention is preferably carried out using crude pyrrolidine which has been prepared by a reaction according to the abovementioned equation [1].

The use of the process of the present invention makes it possible not only to save a distillation step but also to omit dewatering of the crude pyrrolidine with sodium hydroxide.

A prior dewatering step using sodium hydroxide is possible according to the present invention, but is superfluous. A batchwise distillation under reduced pressure is likewise possible, but in this case a prior dewatering step is always necessary in order to obtain in-specification pyrrolidine.

A further advantage of the process of the invention is the high pyrrolidine yield of at least 90% based on crude pyrrolidine used, which was hitherto achievable only using a multistage process. Finally, the process of the present invention has all the advantages of a continuous process, for example constant product quality and low maintenance requirement. This considerably simplifies quality control.

In a further embodiment of the process of the present invention, a pressure at the top of less than 500 hPa, preferably from 200 to 350 hPa, in particular from 250 to 350 hPa, is employed.

A column which can be used for the purposes of the present invention preferably has from about 30 to 40 theoretical plates of which equal numbers are present in the stripping and rectifying sections.

In a further preferred embodiment of the process of the present invention, a reflux ratio of from 3:1 to 10:1 (preferably from 4:1 to 6:1) is set. The reflux ratio to be chosen depends on the number of theoretical plates in the column and is preferably 5:1 in the case of 32 theoretical plates. Such a column is preferably operated at 300 hPa. The invention is illustrated by the following example.

EXAMPLE 1

Crude pyrrolidine having the composition shown in Table 1 is continuously fed into a column having 32 theoretical plates of which 16 are present in the stripping section and 16 are present in the rectifying section.

TABLE I

| Components | % (m/m) determined by GC | g/h determined by GC |
|---|---|---|
| First runnings | 0.15 | 0.5 |
| Pyrrolidine | 48.19 | 168.7 |
| Intermediate runnings | 0.05 | 0.2 |
| Aminobutylpyrrolidine | 0.68 | 2.4 |
| Dipyrrolidinobutane | 7.84 | 27.4 |
| Hydroxybutylpyrrolidine | 0.57 | 2.0 |
| Tails | 3.52 | 12.3 |
| Water | 39.00 | 136.5 |

A reflux ratio of 5:1 was set. The temperature at the top and bottom offtakes was 54–55° and 71–73°, respectively. At the top, a liquid having the composition shown in Table 2 was taken off at a rate of 160 g/h.

TABLE 2

| Components | % (m/m) determined by GC | g/h determined by GC |
|---|---|---|
| First runnings | 0.44 | 0.7 |
| Pyrrolidine | 99.39 | 159.1 |
| Intermediate runnings | 0.02 | — |
| Aminobutylpyrrolidine | — | — |
| Dipyrrolidinobutane | — | — |
| Hydroxybutylpyrrolidine | — | — |
| Tails | — | — |
| Water | 0.15 | 0.2 |

First runnings: Total of the components having shorter retention times than pyrrolidine in the gas chromatogram.

Intermediate runnings: Total components having retention times between those of pyrrolidine and of aminobutylpyrrolidine in the gas chromatogram.

Tails: Total components having higher retention times than hydroxybutylpyrrolidine in the gas chromatogram.

At the bottom, a liquid having the composition shown in Table 3 was taken off at a rate of 190 g/h.

TABLE 3

| Components | % (m/m) determined by GC | g/h determined by GC |
|---|---|---|
| First runnings | — | — |
| Pyrrolidine | 5.45 | 10.4 |
| Intermediate runnings | 0.12 | 0.2 |
| Aminobutylpyrrolidine | 1.42 | 2.7 |
| Dipyrrolidinobutane | 14.76 | 28.0 |
| Hydroxybutylpyrrolidine | 1.25 | 2.4 |
| Tails | 8.9 | 16.9 |
| Water | 68.10 | 129.4 |

The distillation yield was 94%.

We claim:

1. A process for purifying crude pyrrolidine to give a pyrrolidine composition comprising more than 99% (m/m) of pyrrolidine and less than 0.3% (m/m) of water, wherein crude pyrrolidine comprising from 40 to 98% (m/m) of pyrrolidine and having a water content of more than 2% (m/m) is subjected to continuous distillation at a pressure at the top of less than 950 hPa in a column having a stripping section and a rectifying section.

2. A process as claimed in claim 1, wherein a pressure at the top of less than 500 hPa is employed.

3. A process as claimed in claim 2, wherein a pressure at the top of from 200 to 400 hPa is employed.

4. A process as claimed in claim 3, wherein a pressure at the top of from 250 to 350 hPa is employed.

5. A process as claimed in claim 1, wherein the place at which the mixture to be fractionated is fed in is selected so that the number of theoretical plates in the stripping section is the same as that in the rectifying section.

6. A process as claimed in claim 1, wherein a reflux ratio of from 3: 1 to 10:1 is set.

* * * * *